United States Patent
Rovira Soriano et al.

(10) Patent No.: US 10,765,302 B2
(45) Date of Patent: Sep. 8, 2020

(54) CONVERTER DEVICE FOR LARYNGOSCOPY

(71) Applicants: AIMPLAS ASOCIACIÓN DE INVESTIGACIÓN DE MATERIALES PLÁSTICOS Y CONEXAS, Paterna (Valencia) (ES); FUNDACIÓN PARA LA INVESTIGACIÓN DEL HOSPITAL UNIVERSITARIO Y POLITÉCNICO LA FE DE, Valencia (ES)

(72) Inventors: Lucas Rovira Soriano, Valencia (ES); Vicente Ruedas Abarca, Paterna (ES)

(73) Assignees: AIMPLAS ASOCIACIÓN DE INVESTIGACIÒN DE MATERIALES PLÁSTICOS Y CONEXAS, Paterna (ES); FUNDACIÓN PARA LA INVESTIGACIÓN DEL HOSPITAL UNIVERSITARIO Y POLITÉCNICO LA FE DE LA COMUNIDAD VALENCIANA, Valencia (ES)

( * ) Notice: Subject to any disclaimer, the term of this patent is extended or adjusted under 35 U.S.C. 154(b) by 0 days.

(21) Appl. No.: 16/320,979

(22) PCT Filed: Jul. 27, 2017

(86) PCT No.: PCT/ES2017/070540
§ 371 (c)(1),
(2) Date: Jan. 25, 2019

(87) PCT Pub. No.: WO2018/020073
PCT Pub. Date: Feb. 1, 2018

(65) Prior Publication Data
US 2019/0174991 A1 Jun. 13, 2019

(30) Foreign Application Priority Data

Jul. 28, 2016 (ES) .............................. U 201630976

(51) Int. Cl.
*A61B 1/267* (2006.01)
*A61B 1/00* (2006.01)
(Continued)

(52) U.S. Cl.
CPC ............ *A61B 1/0014* (2013.01); *A61B 1/053* (2013.01); *A61B 1/06* (2013.01); *A61B 1/267* (2013.01); *A61B 1/2673* (2013.01)

(58) Field of Classification Search
CPC ......... A61B 1/0014; A61B 1/053; A61B 1/06; A61B 1/267; A61B 1/2673
(Continued)

(56) References Cited

U.S. PATENT DOCUMENTS 3,435,820 A * 4/1969 Stanley ................ A61B 1/0676
600/104
3,884,222 A 5/1975 Moore
(Continued)

FOREIGN PATENT DOCUMENTS

GB 2481585 A 1/2012

OTHER PUBLICATIONS

International Search Report dated Dec. 5, 2017 for PCT Application No. PCT/ES2017/070540, 4 pages.

*Primary Examiner* — Pedro Philogene
*Assistant Examiner* — David C Comstock
(74) *Attorney, Agent, or Firm* — Squire Patton Boggs (US) LLP

(57) ABSTRACT

A converter device for a laryngoscope intended to be linked to a blade (6) of a laryngoscope, having a straight section (7) and a curved section (8), along with a light source (14)
(Continued)

typical of the laryngoscope, for providing it with an additional viewing system in tracheal intubation procedures. The device comprises a central body (1) of tubular section with a through hole (2) for housing an imaging system (3), an upper wing (4) which can be coupled to the curved section (8) of the blade (6), provided with an elastic adjustment portion (11) for adapting to the curved section (8) of the blade (6), and a fastening portion (12) for preventing lateral movement and movement of the device, and a lower wing (5) which can be coupled on the straight section (7) of the blade (6) with an elastic fastening section (13) for adapting to the edge of said straight section (7).

19 Claims, 2 Drawing Sheets

(51) Int. Cl.
*A61B 1/05* (2006.01)
*A61B 1/06* (2006.01)

(58) Field of Classification Search
USPC .................. 600/188, 190, 193, 194, 199
See application file for complete search history.

(56) References Cited

U.S. PATENT DOCUMENTS

| | | | | |
|---|---|---|---|---|
| 4,947,829 | A * | 8/1990 | Bullard | A61B 1/267 600/101 |
| 10,426,567 | B2 * | 10/2019 | McGuire | A61B 17/0206 |
| 2006/0254595 | A1 | 11/2006 | Rea | |
| 2010/0249513 | A1 | 9/2010 | Tydlaska | |
| 2010/0261967 | A1 | 10/2010 | Pacey et al. | |
| 2012/0041268 | A1 * | 2/2012 | Grey | A61B 90/30 600/199 |
| 2014/0323811 | A1 * | 10/2014 | DeSantis | A61B 1/06 600/213 |

* cited by examiner

CONVERTER DEVICE FOR LARYNGOSCOPY

OBJECT OF THE INVENTION

The present invention falls within the technical field of instruments for the medical examination of body cavities, more specifically to instruments for examining the respiratory tract, and relates in particular to a device that can be coupled to the blade of a laryngoscope in order to improve viewing of the larynx and the vocal cords.

BACKGROUND OF THE INVENTION

Many medical specialists, as well as paramedical personnel, face situations on a daily basis in which they need to perform an orotracheal intubation, also known as OTI, which consists of inserting a plastic tube between the vocal cords in order to ensure a correct sealing of the airways and adequate ventilation and oxygenation of the patients. To perform this technique it is necessary to use a conventional laryngoscope, as well as to learn how to perform a procedure know as direct laryngoscopy.

Direct laryngoscopy consists of using the blade of a laryngoscope, inserting it into the mouth of the individual and sliding it down the tongue, using the blade to pull the lower maxilla from the oropharyngeal cavity and thus aligning the tracheal axis with the pharyngeal and oral axes, thus exposing the epiglottis and the glottis. By means of tunnel vision, the vocal cords are viewed, facilitating the passage of the orotracheal tube therethrough.

On occasions, the procedure of intubation is made difficult by not correctly viewing the vocal cords, through which the tube must pass, leading to what is known as patients with difficult airways. It must be emphasized that many of these difficult airways are not known until the orotracheal intubation procedure is performed for the first time, making them unknown and unforeseeable.

In order to overcome these difficulties, different devices have been developed to facilitate orotracheal intubation. Among these devices are video laryngoscopes, which are devices similar to laryngoscopes and that incorporate an optical system in order to facilitate tracheal intubation, providing a better vision of the vocal cords. Several models exist, all of which facilitate intubation by improving the field of vision of the airway. In a conventional laryngoscope, used in direct laryngoscopy, the viewing angle is 15°, while in video laryngoscopes the viewing angle can be increased up to 60°.

However, these devices have high costs and, therefore, in most hospitals there is usually a limited amount of these devices, which are rotated through operating rooms or used for services requiring said devices, and therefore they are not always available. Furthermore, they usually consist of different parts, such as integrated monitors, which hinder their portability and limit their mobility.

It is also worth noting that a video laryngoscope provides an indirect vision of the glottis, which means that the difficulty in using these devices does not strive in being able to view the vocal cords, but rather in managing to direct the endotracheal tube through the vocal cords which are being viewed, a procedure for which there is a learning curve, which is different for each video laryngoscope.

DESCRIPTION OF THE INVENTION

The object of the invention consists of a converter device intended to be linked to the blade of a conventional laryngoscope which currently exists, preferably in those comprising a Macintosh-type blade, in order to provide it with a viewing system which allows improving the vision of the vocal cords and the larynx in a similar way to that of video laryngoscopes, yet without the drawbacks of said video laryngoscopes, which have been previously described.

Laryngoscopes with Macintosh blades have a parabolic curve with a straight distal third, which is the distance between the teeth and the vocal cords, and they allow the tip of the device to be placed in the angle formed by the epiglottis and the base of the tongue.

The device, of smaller dimensions, comprises a central section or socket, of essentially tubular geometry, intended to house an imaging system, which is either optical or electronic. From the lateral faces of said central body, one upper wing and one lower wing extend, intended to be linked to the blade of the laryngoscope and therefore they have a geometry that allows adequate coupling. In order to be able to adapt to different sized blades, it is envisaged that at least one portion of each of said wings is made of a flexible material.

In an alternative embodiment, the central body incorporates an imaging system encapsulated in said device, which is preferably a low-cost micro camera with USB connection. Said integration of the imaging system allows reducing the thickness of said central body.

The device is designed to be easily adapted to the many different types of laryngoscope blades currently on the market. Therefore, variations in the design are envisaged, which include a combination of two plastic materials, one being rigid and the other being more flexible, in order to provide said versatility to the design. Furthermore, the solution designed for viewing the image, according to the variant used, allows connecting fiberscopes with diameters of 5 and 7 mm, or USB micro cameras, which in turn can be connected to different viewing devices.

The design enables obtaining a video laryngoscope, which does not increase the thickness of the blade to which it is coupled in the first third thereof, allowing it to be used in difficult airways. By using a conventional laryngoscope, aligning the axes during the intubation procedure, the passage of the tube through the vocal cords is facilitated without the need to use new additional procedures to improve the intubation rate, which is why the learning curve is simpler. However, with respect to the direct vision obtained with a conventional laryngoscope, which is approximately 15 degrees, the device enables increasing vision indirectly by up to 45°-60°, depending on the patient, given that the viewing angle increases by separating the viewing area from the blade by a few millimeters.

The device has a very low cost compared to other video laryngoscopes, since it is based on technologies previously existing in the operating room. The low volume, along with the easy assembly and the precision in placement, make the device highly portable, light and compact. In addition, it allows using different imaging systems, from fiber optic systems to photoelectric systems, such as USB micro cameras, and allows a high degree of versatility when displaying the image, which may be shown directly on the laparoscopy towers, on monitors, laptop computers, smartphones, digital tablets, etc.

DESCRIPTION OF THE DRAWINGS

As a complement to the description provided herein and for the purpose of helping to make the characteristics of the invention more readily understandable, in accordance with a preferred practical embodiment thereof, said description is accompanied by a set of drawings constituting an integral part of the same, which by way of illustration and not limitation represent the following.

PREFERRED EMBODIMENT OF THE INVENTION

What follows is a detailed description, with the help of the figures referenced above, of a first preferred embodiment of the object of the present invention.

Figure 1:
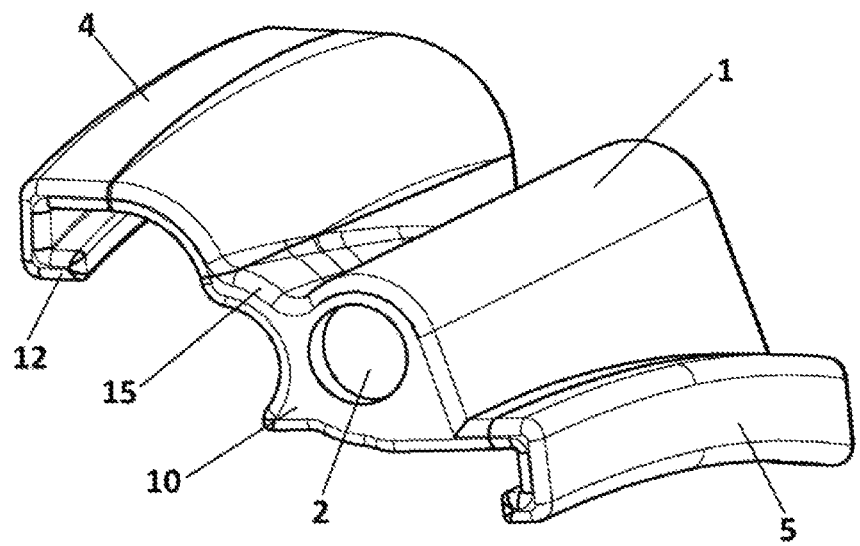
FIG. 1 shows a top perspective view of the converter device for a laryngoscope, in which the main constituting elements thereof can be seen.

The converter device for a laryngoscope described herein is made up of a central body (1) or socket, of essentially tubular geometry, comprising a central hole (2) intended for housing an imaging system (3), micro camera or similar, such as, for example, the distal section of a fiberscope. From each of the lateral faces of said central body (1), one upper wing (4) and one lower wing (5) extend, as shown in FIG. 1, intended to be linked to a blade (6) of the laryngoscope for which they have a geometry that allows adequate coupling. Said blade (6), of the type known as Macintosh blades, comprises a straight section (7) and a curved section (8), perpendicular to one of the longitudinal edges of the straight section (7), so that the upper wing (4) is linked to the curved section (8), while the lower wing (5) is linked to the straight segment (7).

Figure 2:
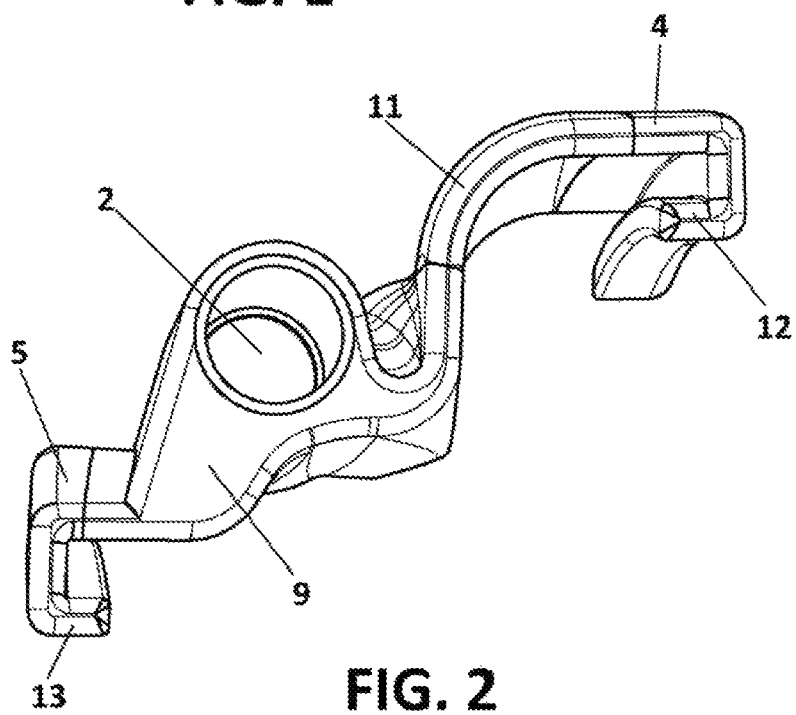
FIG. 2 shows a front view of the back of the device.

Both the central body (1) and the corresponding hole (2) thereof comprise a back end (9), shown in FIG. 2, through which the body of the imaging system (3) is inserted, and a front end (10), with smaller diameters to those of the back end (9) through which the tip of said imaging system (3) passes and in which it is retained due to the reduced dimensions of the front end (10), preventing the same from escaping.

It is envisaged that the interior of the hole (2) further comprises a coating, not shown in the attached figures, which prevents the displacement of the imaging system (3) once inserted into the hole (2). To this end, said coating is made of a material with low density and high friction, such as polyethylene.

The upper wing (4) first comprises an adjustment portion (11) made of an elastic material, which enables it to be adapted to the curved section (8) of the blade (6) of the laryngoscopes. Likewise, the upper wing (4) comprises a fastening portion (12), which prevents lateral and anteroposterior movement of the device once anchored to the laryngoscope.

In the preferred embodiment described herein, the adjustment portion (11) is an intermediate portion of the upper wing (4) with a curved geometry, while the fastening portion (12) has a double L-shaped configuration.

The lower wing (5), in turn, comprises a fastening section (13) for adapting it to the edge of the straight section (7), which has a double L-shaped geometry.

Figure 3:
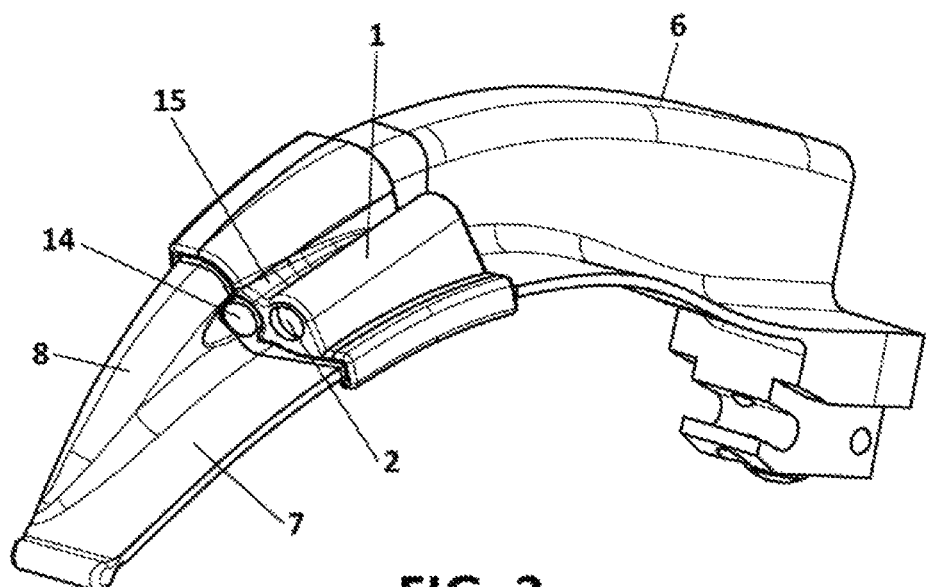
FIG. 3 shows a perspective view of the device coupled to a laryngoscope.

As shown in FIG. 3, the device is intended to be linked to the blade (6) at the point where a light source (14) typical of the laryngoscope is located, releasing the entire front end of said blade (6), which is the part that comes into contact with the tongue and the floor of the mouth of the individual undergoing examination. The upper wing (4) has a notch (15) for passing said light source (14) and thus being able to take advantage of the light produced for better visual display.

Figure 4:
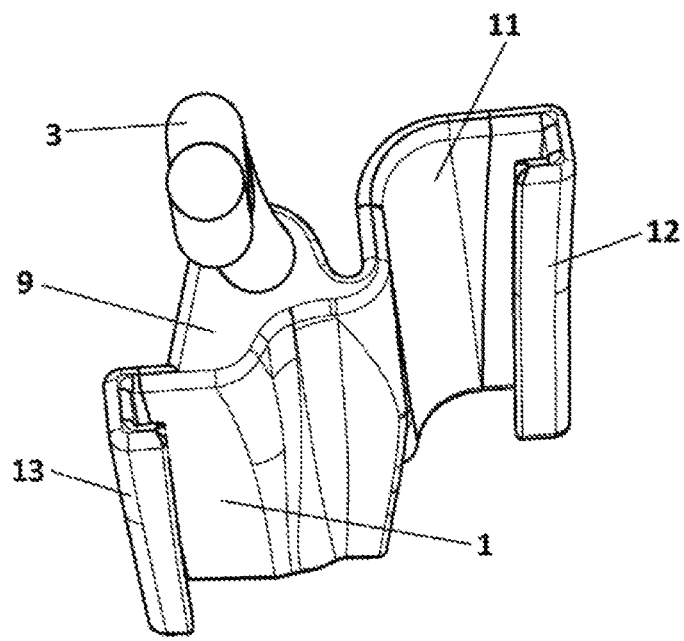
FIG. 4 shows a lower rear perspective view of the converter device according to a second preferred embodiment, incorporating an integrated imaging system.

In a second preferred embodiment, shown in FIG. 4, the imaging system (3) is embedded inside the central body (1) of the device, thereby making it possible to reduce the dimensions of said central body (1), facilitating the orotracheal intubation procedure. In this second preferred embodiment, the imaging system (3) comprises a micro camera with a diameter smaller than 5.5 mm and a CMOS-type sensor of 640×480 pixels, from which a data transmission cable is connected to an external computing device, not shown in the attached figures. Said computing device is provided with specific software, which allows continuous viewing of the images of the glottic structures obtained by the micro camera.

The invention claimed is:

1. A converter device for a tracheal intubation laryngoscope, the laryngoscope comprising a blade having a straight section and a curved section and a light source, for providing a viewing system to facilitate the visualization of the vocal cords and the glottis in tracheal intubation procedures, the converter device being configured to be coupled to the blade of the laryngoscope and comprising:
    a central body of a substantially tubular geometry, comprising a through hole configured to receive an imaging system,
    an upper wing departing from a side of the central body and configured to be coupled to the curved section of the blade, the upper wing comprising:
        an adjustment portion made of an elastic material adaptable to the curved section of the blade, and
        a fastening portion for preventing lateral and anteroposterior movement of the converter device once anchored to the laryngoscope, and
    a lower wing departing from the other side of the central body and configured to be coupled on the straight section of the blade, comprising a fastening section made of an elastic material adaptable to an edge of the straight section.

2. The converter device for a laryngoscope according to claim 1, wherein the adjustment portion of the upper wing is an intermediate portion of the upper wing.

3. The converter device for a laryngoscope according to claim 1, wherein the adjustment portion of the upper wing is a curved portion.

4. The converter device for a laryngoscope according to claim 1, wherein the fastening portion of the upper wing has a double L-shaped configuration.

5. The converter device for a laryngoscope according to claim 1, wherein the fastening section of the lower wing has a double L-shaped configuration.

6. The converter device for a laryngoscope according to claim 1, wherein the upper wing comprises a notch configured to receive the light source of the laryngoscope.

7. The converter device for a laryngoscope according to claim 1, wherein the imaging system is embedded inside the central body.

8. The converter device for a laryngoscope according to claim 7, wherein the imaging system comprises a microcamera, a C-MOS sensor and data transmission cable.

9. The converter device for a laryngoscope according to claim 1, wherein the through-hole of the central body is inclined with respect to the lower wing.

10. The converter device for a laryngoscope according to claim 9, wherein a distal end of the laryngoscope extends along a distal end axis and the through-hole extends along a through-hole axis, the through-hole axis intersects the distal end axis at or near the distal end of the laryngoscope when the converter device is coupled to the laryngoscope.

11. The converter device for a laryngoscope according to claim 1, wherein the central body extends from a back end to a front end and wherein a diameter of the through-hole at the back end is greater than a diameter of the through-hole at the front end.

12. The converter device for a laryngoscope according to claim 1, wherein the laryngoscope extends from a proximal end to a distal end and the converter device is configured to be coupled at a distance with respect the distal end corresponding to one third of a length from the proximal end to the distal end of the laryngoscope.

13. A converter device for a tracheal intubation laryngoscope, the laryngoscope comprising a blade having a straight section and a curved section and a light source to facilitate the visualization of the vocal cords and the glottis in tracheal intubation procedures, the converter being configured to be coupled to the blade of the laryngoscope and comprising:
 a central body extending from a back end to a front end of a substantially tubular geometry, comprising a through hole configured to receive an imaging system,
 an upper wing extending from one side of the central body and configured to be coupled to the curved section of the blade, the upper wing comprising:
  an adjustment portion made of an elastic material and configured to be adapted to the curved section of the blade, and
  a fastening portion for preventing lateral and anteroposterior movement of the converter device when the converter device is coupled to the laryngoscope,
  a notch configured to receive the light source of the laryngoscope, and
 a lower wing extending from the other side of the central body and configured to be coupled on the straight section of the blade, comprising a fastening section made of an elastic material and configured to be adapted to an edge of the straight section of the blade.

14. A kit for a tracheal intubation comprising:
 a tracheal intubation laryngoscope extending from a proximal end to a distal end including:
  a blade having a straight section and a curved section to pull a lower maxilla and tongue from an oropharyngeal cavity in a tracheal intubation process; and
  a light source to light up vocal cords and the glottis in a tracheal intubation process,
 a converter device coupled to the laryngoscope and extending from a back end to a front end, the converter device comprising:
  a central body having a substantially tubular geometry and comprising a through hole extending from the back end to the front end and being configured to receive an imaging system,
  an upper wing departing from a side of the central body and coupled to the curved section of the blade, the upper wing comprising:
   an adjustment portion made of an elastic material adapted to the curved section of the blade, and
   a fastening portion for preventing lateral and anteroposterior movement of the converter device with respect to the laryngoscope,
  a lower wing departing from the other side of the central body and coupled to the straight section of the blade, comprising a fastening section made of an elastic material adapted to an edge of said straight section.

15. The kit for a tracheal intubation according to claim 14, wherein the position of the light source of the laryngoscope substantially coincides with the front end of the converter device.

16. The kit for a tracheal intubation according to claim 14, wherein the upper wing comprises a notch receiving the light source of the laryngoscope.

17. The kit for a tracheal intubation according to claim 14, wherein the front end of the converter device is positioned at a distance from the distal end corresponding to one third of a length from the proximal end to the distal end, and the through-hole is inclined towards the distal end of the laryngoscope.

18. The kit for a tracheal intubation according to claim 14, wherein the fastening portion of the upper wing has a double L-shaped configuration enclosing a portion of the curved section of the laryngoscope.

19. The kit for a tracheal intubation according to claim 14, wherein the fastening section of the lower wing has a double L-shaped configuration enclosing a portion of the straight section of the laryngoscope.

* * * * *